United States Patent
Inukai et al.

(10) Patent No.: US 6,406,434 B2
(45) Date of Patent: Jun. 18, 2002

(54) BLOOD-PRESSURE MEASURING APPARATUS FOR PATIENT UNDER BLOOD-DIALYSIS TREATMENT

(75) Inventors: Hidekatsu Inukai, Komaki; Tohru Oka, Ichinomiya, both of (JP)

(73) Assignee: Colin Corporation, Komaki (JP)

( * ) Notice: Subject to any disclaimer, the term of this patent is extended or adjusted under 35 U.S.C. 154(b) by 11 days.

(21) Appl. No.: 09/749,376

(22) Filed: Dec. 28, 2000

(51) Int. Cl.$^7$ ................................................ A61B 5/02
(52) U.S. Cl. ...................................... 600/490; 600/494
(58) Field of Search ................................ 600/490, 494, 600/492, 493, 495, 496, 500, 501, 502, 485, 481

(56) References Cited

U.S. PATENT DOCUMENTS

| | | | | |
|---|---|---|---|---|
| 4,204,545 A | * | 5/1980 | Yamakoshi | 600/493 |
| 4,710,164 A | * | 12/1987 | Levin et al. | 210/646 |
| 4,715,849 A | * | 12/1987 | Gion et al. | 604/540 |
| 5,454,374 A | * | 10/1995 | Omachi | 600/486 |

FOREIGN PATENT DOCUMENTS

| | | | | | |
|---|---|---|---|---|---|
| JP | 04218729 A | * | 8/1992 | | G01G/19/50 |
| JP | 09224915 A | * | 9/1997 | | A61B/5/0215 |

* cited by examiner

Primary Examiner—Kevin Shaver
Assistant Examiner—Navin Natnithithadha
(74) Attorney, Agent, or Firm—Oliff & Berridge, PLC (57) ABSTRACT

An apparatus for iteratively measuring a blood pressure of a living subject who is undergoing a blood-dialysis treatment, including an inflatable cuff which applies a pressing force to a body portion of the subject, a blood-pressure measuring device which measures a blood pressure of the subject by changing the pressing force of the cuff, a starting device for starting the blood-pressure measuring device at a predetermined period in the dialysis duration, so that the blood-pressure measuring device iteratively measures a blood pressure of the subject at the predetermined period, a period memory device which stores, for a plurality of living subjects including the subject, a plurality of sets of predetermined periods each set of which includes respective predetermined periods for a plurality of partial durations of the dialysis duration, an identifying device for identifying the subject, and a selecting device for selecting, from the sets of predetermined periods stored in the period memory device.

5 Claims, 8 Drawing Sheets

| PATIENT NO. | | | | | |
|---|---|---|---|---|---|
| 1 | TB1=60 | | TB2=15 | TB3=60 | |
| 2 | TB1=60 | TB2=15 | | TB3=60 | |
| 3 | TB1=60 | | TB2=15 | TB3=60 | |
| 4 | TB1=15 | TB2=60 | TB3=15 | TB4=60 | |
| ⋮ | | | ⋮ | | |

```
0      60     120    180    240
```
ELAPSED TIME ET(min)

BLOOD-PRESSURE MEASURING APPARATUS FOR PATIENT UNDER BLOOD-DIALYSIS TREATMENT

BACKGROUND OF THE INVENTION

1. Field of the Invention

The present invention relates to an apparatus for iteratively measuring a blood pressure of a living subject who is undergoing a blood-dialysis treatment.

2. Discussion of Related Art

When a patient is undergoing a blood-dialysis treatment, the dynamic condition of his or her circulatory system may largely change and accordingly his or her blood pressure may largely change. The measurement of blood pressure of the patient under the dialysis treatment is usually carried out by not an invasive method in which blood pressure (BP) values can be continuously measured but a so-called Korotkoff-sound-type or oscillometric-type automatic BP measuring apparatus in which a BP value or values are determined based on the change of Korotkoff sounds, or the change of respective amplitudes of heartbeat-synchronous pulses of pulse wave, detected during the change of pressing pressure of a pressing belt (e.g., a cuff) applied to a body portion of the patient. However, each of the conventional automatic BP measuring apparatuses can obtain a BP value or values, only at a predetermined BP-measurement period. Therefore, if the BP values of the patient under the dialysis treatment significantly largely change immediately after the measuring apparatus measures a BP value or values in one BP measuring operation, the apparatus cannot detect any significant changes (e.g., decreases) of the BP values of the patient, until the measuring apparatus performs the following BP measuring operation after the predetermined BP-measurement period, which may be considerably long. On the other hand, if the BP measuring apparatus measures, in the entire duration of the dialysis treatment, a BP value or values at a BP-measurement period which is so short as to be able to detect any abrupt change of the BP values of the patient, the frequency at which the pressing belt presses the body portion of the patient is increased as such, which leads to increasing the burden exerted to the patient and even producing congestion in the body portion, which, in turn, introduces errors into the BP values measured.

Meanwhile, a doctor or a nurse can estimate, from his or her experiences, a specific partial duration, in the entire duration of dialysis treatment, in which the BP values of the patient may largely decrease, i.e., the BP measuring operations should be performed at a short period. Therefore, it has been generally practiced that the doctor or nurse modifies the BP-measurement-start period to a shorter period at a time around the start of the specific partial duration, and returns the shorter period to the initial, longer period at the end of the specific partial duration. In addition, there is known an apparatus which can employ respective BP-measurement-start periods for a plurality of partial durations in the entire duration of dialysis treatment, such that one of the periods that corresponds to a specific partial duration in which BP values of a patient may largely decrease is shorter than the period or periods for the other partial duration or durations.

However, both of the above-described conventional manners of monitoring of BP values are not only cumbersome but also need to employ a long specific duration associated with a short BP-measurement-start period, so that any large decrease of the BP values may assuredly occur in the specific partial duration. This leads to increasing the burden exerted to the patient. Moreover, even in the above manners in which the long specific duration is employed, there are known many cases where the large decrease of BP values occurs in the other duration or durations, in the entire dialysis duration, than the long specific duration and cannot be detected so quickly.

SUMMARY OF THE INVENTION

It is therefore an object of the present invention to provide a blood-pressure measuring apparatus which can measure a blood pressure of a patient who is undergoing a blood-dialysis treatment and which can quickly detect a decrease of the blood pressure of the patient, without exerting large burden to the patient.

In the above-described background, the present inventors have performed extensive studies, and have found that a specific partial duration, in the entire duration of dialysis treatment, in which blood pressure may abruptly decrease occurs depending on individual patients and that if there is the specific partial duration in which the blood pressure abruptly decreases, the specific partial duration is just a limited duration in the entire dialysis duration.

The above object has been achieved by the present invention, which provides an apparatus for iteratively measuring a blood pressure of a living subject who is undergoing a blood-dialysis treatment, comprising an inflatable cuff which applies a pressing force to a body portion of the subject; a blood-pressure measuring device which measures a blood pressure of the subject by changing the pressing force of the cuff applied to the body portion of the subject; a starting means for starting the blood-pressure measuring device at a predetermined period in a dialysis duration in which the subject undergoes the blood-dialysis treatment, so that the blood-pressure measuring device iteratively measures a blood pressure of the subject at the predetermined period; a period memory device which stores, for a plurality of living subjects including the subject, a plurality of sets of predetermined periods each set of which comprises respective predetermined periods for a plurality of partial durations of the dialysis duration; an identifying means for identifying the subject; and a selecting means for selecting, from the sets of predetermined periods stored in the period memory device, the set of predetermined periods for the subject, so that the starting means starts, in each of the partial durations of the dialysis duration, the blood-pressure measuring device at a corresponding one of the predetermined periods of the selected set, and the blood-pressure measuring device iteratively measures a blood pressure of the subject in the each of the partial durations of the dialysis duration at the corresponding one of the predetermined periods of the selected set.

In the present BP measuring apparatus, the identifying means identifies the subject, the selecting means selects, from the sets of predetermined periods stored in the period memory device, the set of predetermined periods for the subject, the starting means starts, in each of the partial durations of the dialysis duration, the blood-pressure measuring device at a corresponding one of the predetermined periods of the selected set, and the blood-pressure measuring device iteratively measures a blood pressure of the subject in the each of the partial durations at the corresponding one of the predetermined periods. Thus, the dialysis duration can be divided into a plurality of partial durations including at least one specific partial duration in which the BP values of the living subject may largely decrease and which is associated with at least one predetermined period shorter than at least one predetermined period associated with at least one partial duration of the dialysis duration other than the specific partial duration. Therefore, the present apparatus can be easily operated for monitoring the BP values of each individual subject (e.g., patient), and quickly detecting any abrupt decrease of the BP values of the subject, and the length of the specific partial duration can be minimized. which leads to reducing the burden exerted to the subject during the dialysis treatment.

According to a preferred feature of the present invention, the blood-pressure measuring apparatus further comprises a detecting means for detecting a change of the blood pressure values iteratively measured by the blood-pressure measuring device; and a modifying means for modifying, when the detecting means detects the change of the blood pressure values at an elapsed time in a first one of the partial durations of the dialysis duration that is associated with a longer predetermined period than a predetermined period associated with at least one of a second partial duration preceding the first partial duration, and a third partial duration following the first partial duration, the set of predetermined periods selected by the selecting means for the subject, such that the modified set of periods comprises, for a predetermined partial duration including the elapsed time, a period shorter than the longer predetermined period, the modifying means storing, in the period memory device, the modified set of periods in place of the selected set of periods.

In this BP measuring apparatus, the detecting means detects a change of the BP values iteratively measured by the BP measuring device, and the modifying means modifies, when the detecting means detects the change of the BP values at an elapsed time in a first partial duration associated with a longer predetermined period than a predetermined period associated with at least one of a second partial duration preceding the first partial duration, and a third partial duration following the first partial duration, the set of predetermined periods selected by the selecting means for the subject, such that the modified set of periods includes, for a predetermined partial duration including the elapsed time, a period shorter than the longer predetermined period, and additionally stores, in the period memory device, the modified set of periods in place of the selected set of periods. Thus, the contents or data stored in the period memory device are automatically modified as the BP values of the subject are iteratively measured by the BP measuring device.

According to another preferred feature of the present invention, the blood-pressure measuring apparatus further comprises a blood-pressure memory device which stores, for the subject, the blood pressure values iteratively measured by the blood-pressure measuring device in the dialysis duration, and respective elapsed times, after a commencement of the dialysis duration, at which the blood pressure values are iteratively measured by the blood-pressure measuring device; and a modifying means for modifying, when the blood pressure values stored in the blood-pressure memory device in the dialysis duration for the subject comprise at least one blood pressure value lower than a reference value, the set of predetermined periods selected by the selecting means for the subject, such that the modified set of periods comprises, for at least one first predetermined partial duration including at least one elapsed time corresponding to the at least one blood pressure value, a first predetermined period shorter than a second predetermined period for at least one second partial duration of the dialysis duration other than the at least one first partial duration, the modifying means storing, in the period memory device, the modified set of periods in place of the selected set of periods.

In this BP measuring apparatus, the BP memory device stores, for the subject, the BP values iteratively measured by the BP measuring device in the dialysis duration, and respective elapsed times, after the commencement of the dialysis duration, at which the BP values are iteratively measured, and the modifying means modifies, when the BP values stored in the BP memory device in the dialysis duration for the subject include at least one BP value lower than a reference value, the set of predetermined periods selected by the selecting means for the subject, such that the modified set of periods includes, for at least one first predetermined partial duration including at least one elapsed time corresponding to the at least one blood pressure value, a first predetermined period shorter than a second predetermined period for at least one second partial duration of the dialysis duration other than the at least one first partial duration, and additionally stores, in the period memory device, the modified set of periods in place of the selected set of periods. Thus, the set of predetermined periods and the corresponding partial durations, for the subject, are automatically optimized and stored in the period memory device.

BRIEF DESCRIPTION OF THE DRAWINGS

The above and other objects, features, advantages and technical and industrial significance of the present invention will be better understood by reading the following detailed description of preferred embodiments of the invention, when considered in connection with the accompanying drawings, in which.

DETAILED DESCRIPTION OF PREFERRED EMBODIMENTS

Hereinafter, there will be described a blood-pressure (BP) measuring apparatus 8 as an embodiment of the present invention, by reference to the accompanying drawings.

Figure 1:
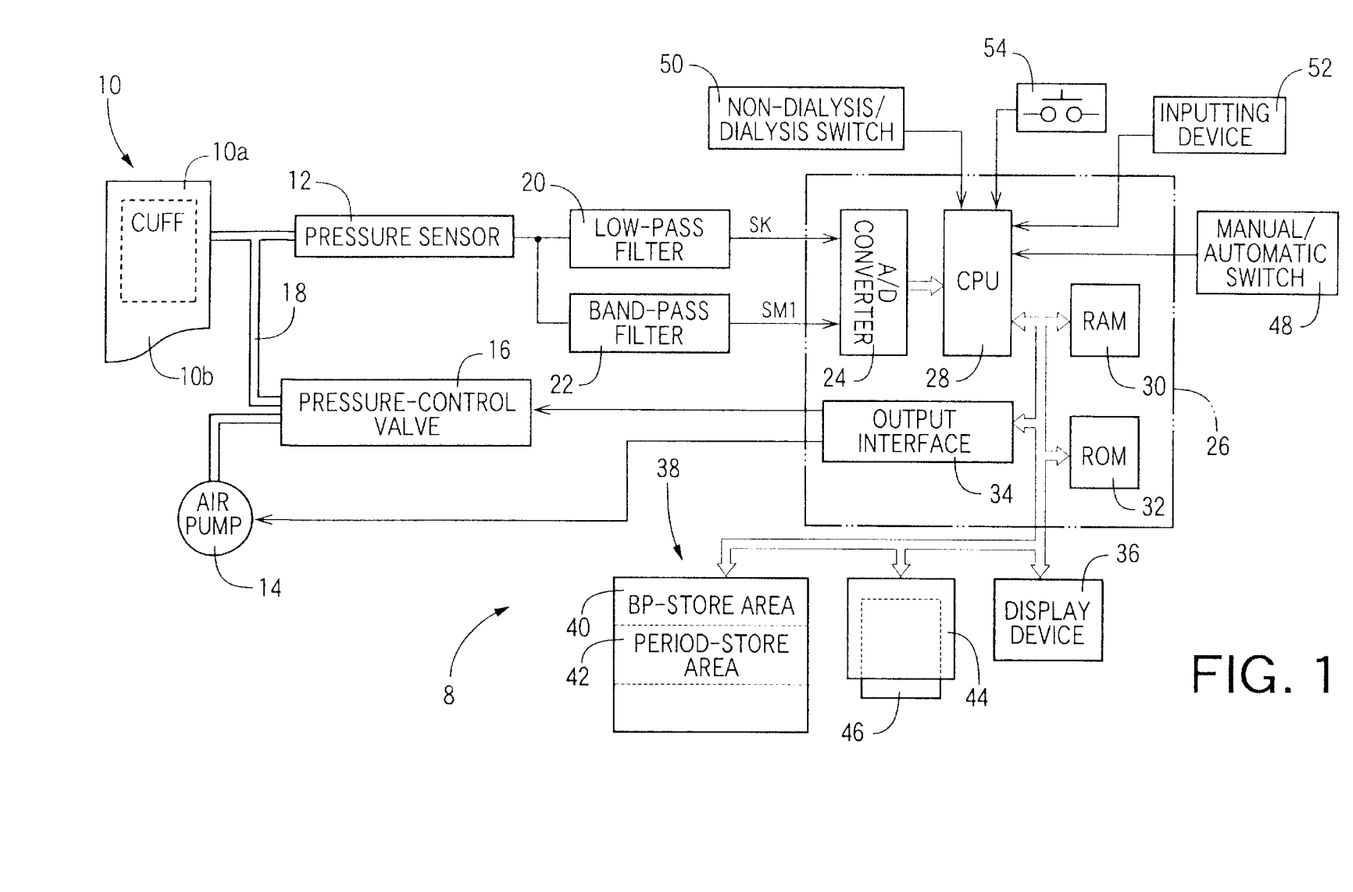
FIG. 1 is a diagrammatic view for explaining the construction of a blood-pressure (BP) measuring apparatus for a patient who undergoes a blood-dialysis treatment, to which the present invention is applied.

FIG. 1 is a diagrammatic view for explaining a construction of the BP measuring apparatus 8, which is used for iteratively measuring a BP value of a patient who is undergoing a blood-dialysis treatment. In FIG. 1, reference numeral 10 designates an inflatable cuff 10 which is wound around an upper arm of the patient for pressing the same. The cuff 10 includes an inflatable bag 10a which is formed of an elastic sheet such as a rubber sheet or a vinyl sheet; and a non-stretchable arm band 10b which accommodates the bag 10a. The bag 10a is connected via an air pipe 18 to a pressure sensor 12, an air pump 14, and a pressure-control valve 16.

The pressure sensor 12 includes a semiconductor pressure-sensitive element which detects an air pressure in the cuff 10 (or the bag 10a) and supplies a pressure signal, SP; representing the detected pressure, to a low-pass filter 20 and a band-pass filter 22. The low-pass filter 20 extracts, from the pressure signal SP, a direct-current component representing a static pressure, Pc, in the cuff 10, and outputs a cuff-pressure signal, SK, representing the static pressure Pc, to an analog-to-digital (A/D) converter 24. The band-pass filter 22 extracts, from the pressure signal SP, an alternate-current component having frequencies of from 1 to 10 Hz, and outputs a pulse-wave signal, SM1, representing the alternate-current or frequency component, to the A/D converter 24. The pulse-wave signal SM1 represents a pulse wave, i.e., a pressure change or oscillation which is produced in the cuff 10, by the pulsation of arteries present in the upper arm under the cuff 10, in synchronism with the heartbeat of the patient.

The band-pass filter 22 has a narrow frequency band which can remove noise, such as motion-artifact noise, from respective amplitudes of successive heartbeat-synchronous pulses of the pulse wave, i.e., the pressure oscillation which is produced in the cuff 10 in synchronism with the heartbeat of the patient. When the pressure in the cuff 10 is gradually changed at a low rate (e.g., 2 to 3 mmHg/sec) in a BP measuring operation, the band-pass filter 22 detects the respective amplitudes of successive heartbeat-synchronous pulses of the pulse wave, and outputs the pulse-wave signal SM1 representing the pulse wave, to the A/D converter 24. The A/D converter 24 includes a multiplexer which receives, by time sharing, the two sorts of input signals SK, SM1, and has the function of concurrently subjecting the two sorts of input signals SK, SM1 to the A/D conversion.

The BP measuring apparatus 8 includes a control device 26 which is provided by a microcomputer including a central processing unit (CPUT) 28, a random access memory (RAM) 30, a read only memory (ROM) 32, and an output interface 34. The CPU 28 processes the input signals supplied from the A/D converter 24, by utilizing the temporary-storage function of the RAM 30, according to the control programs pre-stored in the ROM 32, and controls the respective operations of the air pump 14 and the pressure-control valve 16 via the output interface 34, for measuring, in each BP measuring operation, one or more BP values, BP, of the patient. More specifically described, the control device 26 operates the air pump 14 to increase the air pressure in the cuff 10 and thereby press the upper arm of the patient, subsequently operates the pressure-control valve 16 to decrease slowly the pressure of the cuff 10, and obtains the pulse-wave signal SM1 and the cuff-pressure signal SK during the slow decreasing of the cuff pressure. Then, based on the thus obtained pulse-wave signal SM1 and cuff-pressure signal SK, the control device 26 determines, according to a well-known oscillometric BP-determining algorithm, one or more BP values BP of the patient, and operates a display device 36 to display the thus determined BP value or values BP. In addition, the control device 26 stores, in a BP-store area 40 of a memory device 38, the thus determined BP value BE and an elapsed time, ET, when the BP value BP is determined after the commencement of the current dialysis treatment. The control device 26 iterates the above-described operations in each of BP measuring operations after the commencement of the dialysis treatment. Thus, the control device 26 sequentially stores, in the BP-store area 40, a plurality of combinations of BP value BP and elapsed time ET. The BP-store area 40 functions as a BP memory device. The memory device 38 may be provided by a well known memory such as a magnetic disc or tape or a volatile or non-volatile semiconductor memory.

The memory device 38 additionally includes a period-store area 42 which stores, for each of a plurality of patients, respective BP-measurement-start periods, $T_B$, for a plurality of partial durations obtained by dividing the entire duration of dialysis treatment. The period-store area 42 functions as a period memory device. The CPU 28 identifies each patient based on identification data which are recorded on a magnetic card 46 which is inserted by the patient in a card reader 44, reads out, from the period-store area 42 of the memory device 38, the set of BP-measurement-start periods $T_B$ corresponding to the identified patient, and starts the BP measuring operation at the respective periods $T_B$ in the respective partial durations of the dialysis treatment.

A manual-mode/automatic-mode selecting switch 48 is operated for selecting a manual mode in which the BP measuring operation is started manually by an operator, and an automatic mode in which the BP measuring operation is started automatically by the present apparatus 8, and selectively supplies a first command signal indicating the manual mode, and a second command signal indicating the automatic mode, to the CPU 28. A non-dialysis-mode/dialysis-mode selecting switch 50 is operated for selecting a non-dialysis mode and a dialysis mode, and selectively supplies a first command signal indicating the non-dialysis mode, and a second command signal indicating the dialysis mode, to the CPU 28. In the non-dialysis mode, a BP measuring operation is started periodically at a predetermined period; and in the dialysis mode, the entire duration of dialysis treatment is divided into a plurality of partial durations, and respective BP-measurement-start periods $T_B$ are given to the partial durations, for each patient who is undergoing the dialysis treatment, because each individual patient has his or her specific partial duration in which his or her BP values may largely change.

A period-inputting device 52 is manually operated for inputting (a) a BP-measurement-start period at which a BP measuring operation is started while the non-dialysis-mode/dialysis-mode selecting switch 50 is set at the non-dialysis-mode, and (b) a plurality of partial durations and respective BP-measurement-start periods $T_B$ for the partial durations, so that a BP measuring operation is started at the respective periods $T_B$ in the respective partial durations of the dialysis treatment while the switch 50 is set at the dialysis-mode. The period-inputting device 52 supplies a command signal indicating the input period or periods and/or durations, to the CPU 28. A start/stop switch 54 is operated for starting and stopping the operation of the present BP measuring apparatus 8, and alternately supplies a first command signal indicating a start command and a second command signal indicating a stop command, to the CPU 28, each time the switch 52 is operated.

Figure 2:
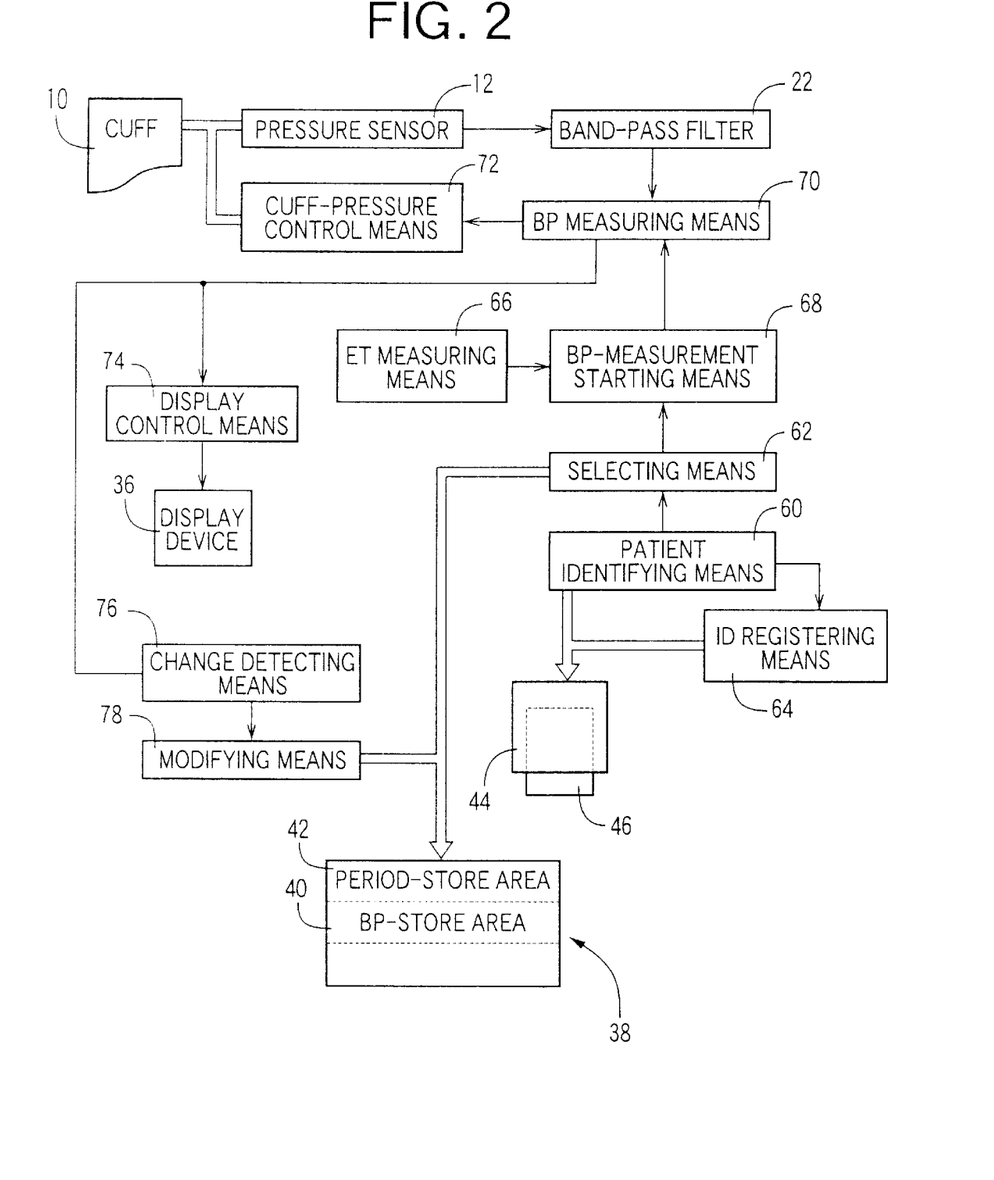
FIG. 2 is a diagrammatic view for explaining various functions of a control device 26 of the BP measuring apparatus.

FIG. 2 is a diagrammatic view for explaining various functions of the control device 26. In FIG. 2, a patient identifying means 60 identifies a patient who undergoes a blood-dialysis treatment, that is, judges whether identification (ID) data identifying the patient are already registered in the period-store area 42 of the memory device 38. More specifically described, the patient identifying means 60 reads in the ID data recorded on the magnetic card 46 inserted by the patient in the card reader 44, and judges whether the read-in ID data are identical with one of a plurality of ID data which are already registered, in the period-store area 42, in association with corresponding sets of BP-measurement-start periods $T_B$.

A period selecting means 62 selects, from the period-store area 42, (a) the partial durations of the dialysis duration, and (b) the set of BP-measurement-start periods $T_B$ corresponding to those partial durations, both of which are registered in the period-store area 42 for the patient identified by the patient identifying means 60. The thus selected partial durations include at least one specific partial duration in which the BP values of the patient may largely change.

Figure 3:
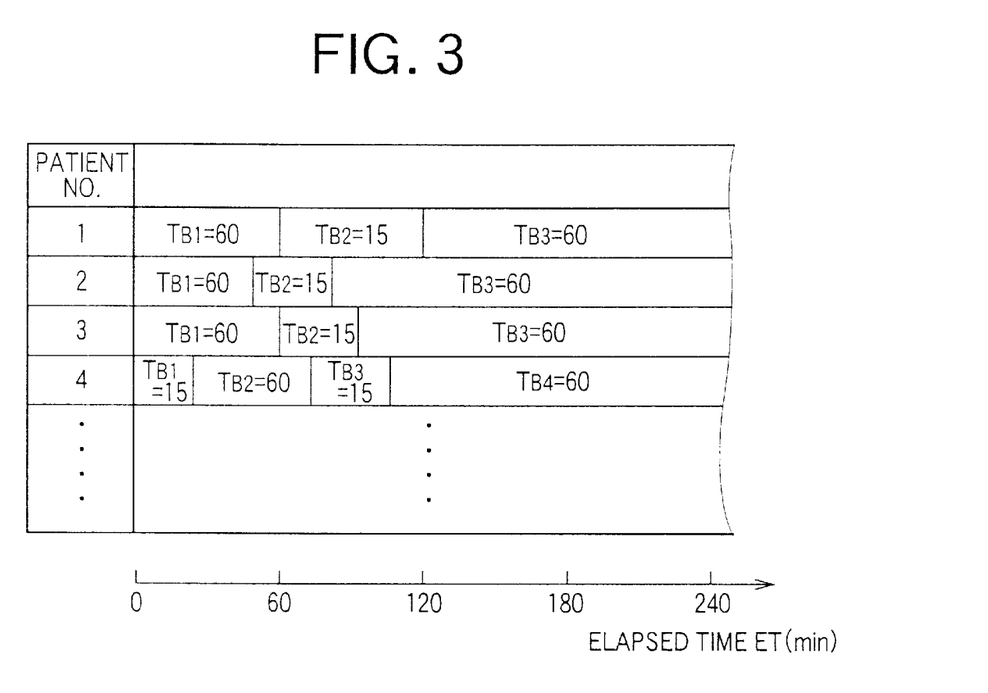
FIG. 3 is a view for explaining a plurality of sets of BP-measurement-start periods $T_B$ which are stored in a period-store area 42 of a memory device 38 of the BP measuring apparatus.

FIG. 3 shows four sets of BP-measurement-start periods $T_B$ for four patients, No. 1, 2, 3, and 4, all of which are stored in the period-store area 42. For example, the period-store area 42 stores, for Patient No. 1 (his or her ID data are 1), a first period, $T_{B1}$, of 60 minutes for a first partial duration of 60 minutes after the commencement of the dialysis treatment; a second period, $T_{B2}$, of 15 minutes for a second partial duration of 60 minutes from the 60 minutes to 120 minutes after the commencement; and a third period, $T_{B3}$, of 60 minutes for a third partial duration from the 120 minutes to the end of the dialysis treatment.

An identification-data (ID-data) registering means 64 registers, when the patient identifying means 60 fails to identify the patient, i.e., when-the period-store area 42 does not have the ID data of the patient, the ID data of the patient that has been read in by the patient identifying means 60 from the magnetic card 46. In the present embodiment, the ID data of the current patient are the total number of the patients, including the current patient, that have been registered by the ID registering means 64. Alternatively, the ID data may be the name of the patient. When the ID-registering means 64 registers the ID data of the patient, a doctor, a nurse, or an operator manually inputs, through the period-inputting device 52, a set of BP-measurement-start periods $T_B$ suitable for the patient, or the control device 26 automatically reads in, from the ROM 32, a standard set of BP-measurement-start periods $T_B$ suitable for many people, so that the manually input or automatically read-in set of periods $T_B$ are stored in the period-store area 42 of the memory device 38.

An elapsed-time (ET) measuring means 66 includes a counter (not shown) which counts the number of clock pulses outputted from a clock circuit (not shown) after the current dialysis treatment is commended in the state in which the manual-mode/automatic-mode selecting switch 48 is set at the automatic mode and the non-dialysis-mode/dialysis-mode selecting switch 50 is set at the dialysis mode. Thus, the ET measuring means 66 measures an elapsed time, ET, which has elapsed after the commencement of the current dialysis treatment.

A BP-measurement starting means 68 starts, in each of the partial durations of the dialysis treatment, a BP measuring operation of a BP measuring means 70, each time the elapsed time ET measured by the ET measuring means 66 increases up to be equal to a corresponding one of the BP-measurement-start periods $T_B$ selected by the period selecting means 62.

A cuff-pressure control means 72 quickly increases the pressing pressure of the cuff 10 wound around the upper arm of the patient, up to a predetermined target value, $P_{CM}$, (e.g., 180 mmHg), and subsequently slowly decreases the cuff pressure at a low rate of 3 mmHg. During this slow deflation of the cuff 10, the BP measuring means 70 collects the respective amplitudes of successive heartbeat-synchronous pulses of the pulse wave represented by the pulse-wave signal SM1, and determines, based on the change of the thus collected pulse amplitudes, a systolic BP value, $BP_{SYS}$, a mean BP value, $BP_{MEAN}$, and a diastolic BP value. $BP_{DIA}$, of the patient, according to the well-known oscillometric BP-determining algorithm.

A display control means 74 controls the display device 36 to display, on a two-dimensional coordinate plane (FIG. 6) defined by a first axis indicative of elapsed time ET (min) and a second axis indicative of BP value BP (mmHg), (a) the BP values BP iteratively measured by the BP measuring means 70 at the respective elapsed times ET measured by the ET measuring means 66 in the entire duration of the dialysis treatment, and (b) a current elapsed time ET measured by the ET measuring means 66.

A change detecting means 76 detects a significant change of the BP values BP iteratively measured by the BP measuring means 70. For example, when the current BP value BP measured by the BP measuring means 70 is lower than a reference pressure value, or when an absolute value of a rate of change of the current BP value from its preceding BP value with respect to time, or an absolute value of a proportion of an amount of change of the current BP value from its preceding BP value with respect to the preceding BP value is greater than a reference value, the change detecting means 76 recognizes or detects it as a significant change of the BP values of the patient.

A modifying means 78 modifies, when the change detecting means 76 detects one significant change of the BP values BP of the patient, at one elapsed time ET in one of the partial durations, selected by the period selecting means 62, that is associated with a longer BP-measurement-start period $T_B$ than that associated with its preceding or following partial duration in the dialysis duration, the set of the BP-measurement-start periods $T_B$ selected by the period selecting means 62, such that the modified set of periods $T_B$ includes, for a predetermined partial duration including the above-indicated one elapsed time ET, a predetermined BP-measurement-start period $T_B$ which is shorter than the above-indicated longer BP-measurement-start period $T_B$ by a predetermined value. The thus modified or new set of periods $T_B$ is stored, in place of the selected set of periods $T_B$, in the period-store area 42 of the memory device 38. In addition, a modified set of partial durations including the above-indicated predetermined partial duration is stored, in place of the selected set of partial durations, in the period-store area 42.

Figure 4:
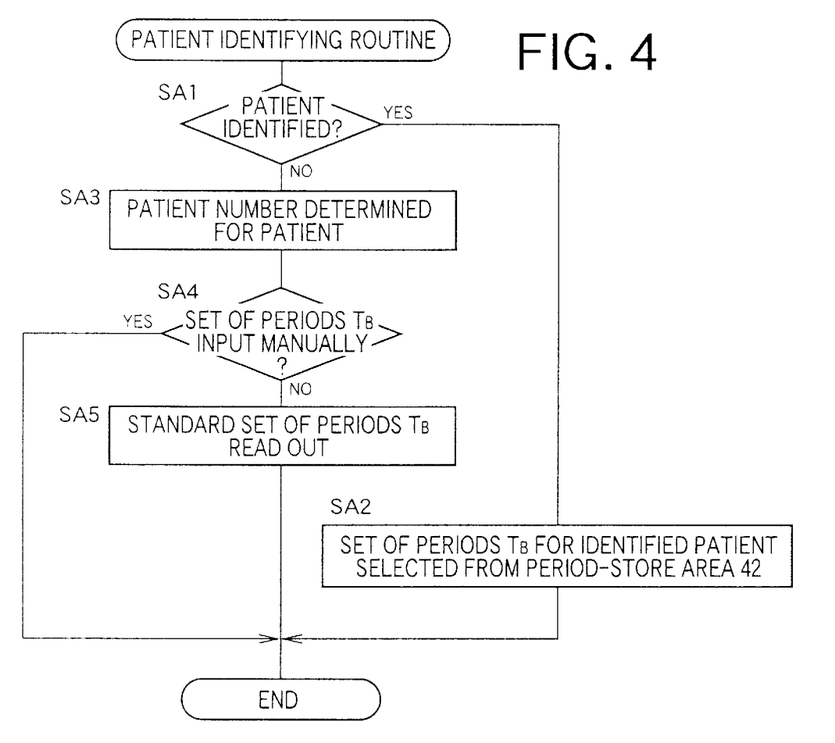
FIG. 4 is a flow chart representing a patient identifying routine according to which the control device 26 operates the BP measuring apparatus for identifying the patient.
Figure 5:
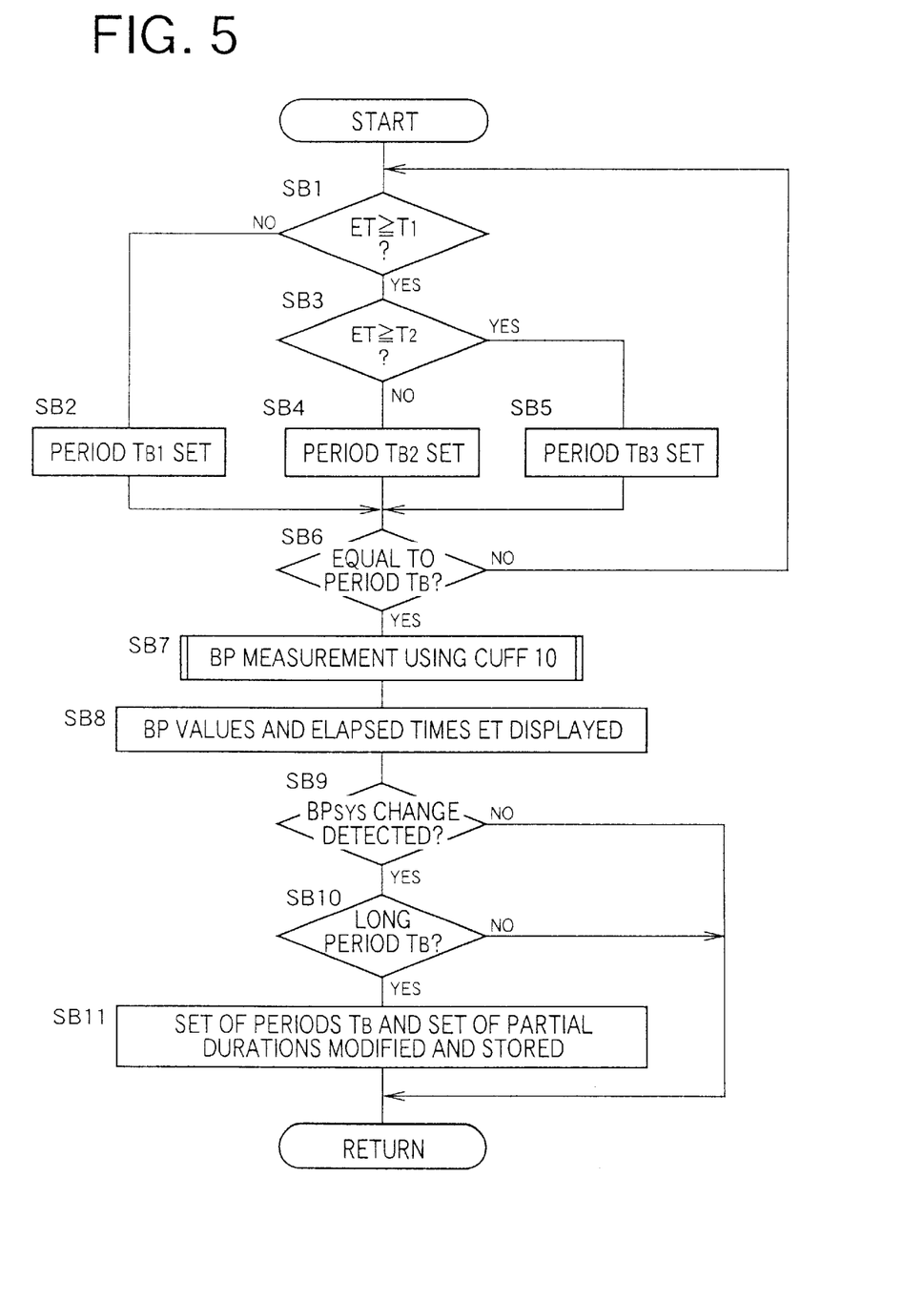
FIG. 5 is a flow chart representing an automatic BP measuring routine according to which the control device 26 operates the BP measuring apparatus for automatically measuring a BP value of the patient.

FIGS. 4 and 5 show two flow charts representing two control programs according to which the control device 26 controls the present BP measuring apparatus 8. FIG. 4 shows a patient identifying routine for identifying a patient and thereby selecting a set of BP-measurement-start periods $T_B$ for the patient; and FIG. 5 shows an automatic BP-measuring routine for automatically starting the BP measuring apparatus 8 or the BP measuring means 70 at each of the selected periods $T_B$. The two routines are carried out only while the manual-mode/ automatic-mode selecting switch 48 is set at the automatic mode.

At Step SA1 of FIG. 4 corresponding to the patient identifying means 60, the control device 26 judges whether the magnetic card 46 which has been inserted by the current patient in the card reader 44 has ID data indicating a patient number allotted to the current patient and, if the card 46 has the ID data or the patient number, judges whether the patient number is identical with one of the patient numbers which has been stored in the period-store area 42 of the memory device 38.

If a positive judgment is made at Step SA1, the control goes to Step SA2 corresponding to the period selecting means 62. At Step SA2, the control device 26 selects, from the period-store area 42, the set of BP-measurement-start periods $T_B$ which is associated with the one patient number identical with the patient number recorded on the magnetic card 46. Thus, the current control cycle according to the routine of FIG. 4 is terminated.

On the other hand, if a negative judgment is made at Step SA1, the control goes to Step SA3 corresponding to the ID registering means 64. At Step SA3, the control device 26 determines, as a patient number of the current patient, the total number of the patients who have been registered in the period-store area 42, including the current patient, and additionally records, on the magnetic card 46, the thus determined patient number as ID data identifying the current patient.

Step SA3 is followed by Step SA4. When the control device 26 determines and allots the patient number to the current patient at Step SA3, the period-store area 42 of the memory device 38 has not stored a set of BP-measurement-start periods $T_B$ for the current patient having the patient number. Therefore, at Step SA4 or Step SA5, a set of BP-measurement-start periods $T_B$ is manually input through the inputting device 52, or is automatically read out from the ROM 32.

More specifically described, at Step SA4, the control device 26 judges whether a set of BP-measurement-start periods $T_B$ for a set of partial durations of the entire duration of dialysis treatment have been input through manual operation of the inputting device 52, i.e., whether a set of BP-measurement-start periods $T_B$ and a set of partial durations which have been manually input through the inputting device 52 have been registered in the period-store area 42. If a positive judgment is made at Step SA4, the current control cycle is ended. On the other hand, if a negative judgment is made at Step SA4, the control goes to Step SA5 at which the control device 26 reads, from the ROM 32, a standard set of BP-measurement-start periods, $ST_B$, for a standard set of partial durations of the dialysis duration, and then the current control cycle is ended. The standard set of partial durations includes a considerably long specific duration associated with a short BP-measurement-start period $T_B$, SO that any abrupt decrease of BP values can be quickly detected for many patients.

The patient identifying routine of FIG. 4 is followed by the automatic BP-measuring routine of FIG. 5. Here, it is assumed that the set of BP-measurement-start periods $T_B$, $ST_B$ and the set of partial durations of the dialysis duration that have been selected, input, or read at Step SA2, SA4, or SA5 include three periods and three partial durations.

First, at Step SB1 of FIG. 5, the control device 26 judges whether the elapsed time ET measured after the commencement of the current dialysis treatment increases up to be equal to, or greater than, a first reference time, $T_1$. The first reference time $T_1$ is the time of end of the first partial duration of the partial durations selected, input, or read at Step SA2, SA4, or SA5, i.e., the start of the second partial duration. If the current patient is, for example, Patient No. 1 shown in FIG. 3, the first reference time $T_1$ is 60 minutes after the commencement of the dialysis treatment.

If a negative judgment is made at Step SB1, the control goes to Step SB2 to set, for the first partial duration, a first BP-measurement-start period $T_{B1}$ of the BP-measurement-start periods $T_B$, $ST_B$ selected, input, or read at Step SA2, SA4, or SA5. Regarding Patient No. 1, the first BP-measurement-start period $T_{B1}$ is 60 minutes. On the other hand, if a positive judgment is made at Step SB1, the control goes to Step SB3 at which the control device 26 judges whether the elapsed time ET measured increases up to be equal to, or greater than, a second reference time, $T_2$. The second reference time $T_2$ is the time of end of the second partial duration, i.e., the start of the third partial duration. Regarding Patient No. 1, the second reference time $T_2$ is 120 minutes after the commencement of the dialysis treatment.

If a negative judgment is made at Step SB3, the control goes to Step SB4 to set, for the second partial duration, a second BP-measurement-start period $T_{B2}$ of the BP-measurement-start periods $T_B$, $ST_B$ selected, input, or read at Step SA2, SA4, or SA5. Regarding Patient No. 1, the second BP-measurement-start period $T_{B2}$ is 15 minutes. On the other hand, if a positive judgment is made at Step SB3, the control goes to Step SB5 to set, for the third partial duration, a third BP-measurement-start period $T_{B3}$ of the BP-measurement-start periods TB, STB selected, input, or read at Step SA2, SA4, or SA5. Regarding Patient No. 1, the third BP-measurement-start period $T_{B3}$ is 60 minutes.

Step SB2, SB4, or SB5 is followed by Step SB6 corresponding to the BP-measurement starting means 68. At Step SB6, the control device 26 judges whether a time which has elapsed from the last BP measurement using the cuff 10 at Step SB7, described below, has increased up to be equal to the BP-measurement-start period TB set at Step SB2, SB4, or SB5. If a negative judgment is made at Step SB6, the control goes back to Step SB1 and the following steps. On the other hand, if a positive judgment is made at Step SB6, the control goes to Step SB7 corresponding to the BP measuring means 70. At Step SB7, the control device 26 carries out a BP measuring operation using the cuff 10, and determines a systolic BP value $BP_{SYS}$, a mean BP value $BP_{MEAN}$, and a diastolic BP value $BP_{DIA}$.

Figure 6:
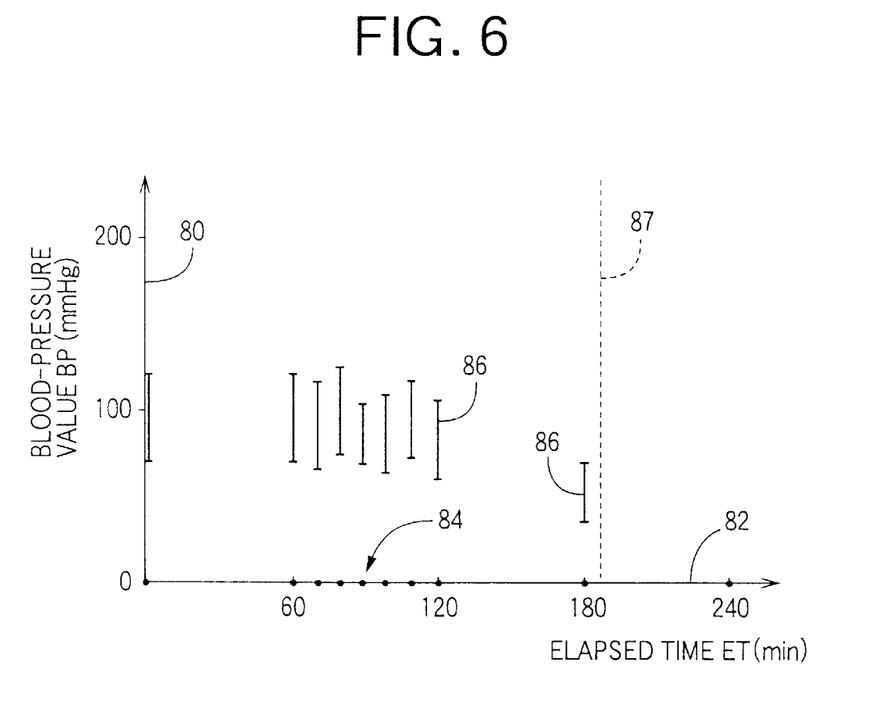
FIG. 6 is a view showing (a) a plurality of BP values BP measured by the BP measuring apparatus at respective elapsed times ET, and (b) a current elapsed time ET, all of which are displayed on a display device 36 of the BP measuring apparatus.

Step SB7 is followed by Step SB8 corresponding to the display control means 74. At Step SB8, the control device 26 controls the display device 36 to display, on the two-dimensional coordinate plane defined by the first axis 82 indicative of elapsed time ET and the second axis 80 indicative of BP value BP, the BP values BP determined at Step SB7, at the respective elapsed times ET measured by the ET measuring means 66. FIG. 6 shows the BP values BP and the elapsed times ET which are displayed, for Patient No. 1, on the display device 36. Black circles 84 indicate the elapsed times ET, such that the black circle 84 in the first partial duration from 0 to 60 minutes is obtained at the first period $T_{B1}$ of 60 minutes, the black circles 84 in the second partial duration from 60 to 120 minutes are obtained at the second period $T_{B2}$ of 15 minutes, and the black circles 84 in the third partial duration after 120 minutes are obtained at the third period $T_{B3}$ of 60 minutes. Vertical bars 86 are plotted, along the first axis 82, at respective positions indicated by the respective black circles 84 indicating the respective elapsed times ET corresponding to the BP values BP indicated by the vertical bars 86. A top end and a bottom end of each vertical bar 86 indicate a systolic BP value $BP_{SYS}$ and a diastolic BP value $BP_{DIA}$, respectively, and a length of the each vertical bar 86 indicates a difference between the systolic and diastolic BP value $BP_{SYS}$, $BP_{DIA}$. A broken line 87 indicates a current elapsed time ET measured by the ET measuring means 66.

Next, at Step SB9 corresponding to the change detecting means 76, the control device 26 calculates an absolute value, %BP$_{SYS}$, of a proportion of an amount of change of the current systolic BP value, BP$_{SYSn}$, determined at Step SB7 in the current (i.e., n-th) control cycle from the preceding systolic BP value, BP$_{SYSn-1}$, determined at Step SB7 in the preceding (i.e., (n−1)-th) control cycle, to the preceding systolic BP value BP$_{SYSn-1}$, and judges whether the thus calculated value %BP$_{SYS}$ is not smaller than 20%, that is, %BP$_{SYS}$(=(BP$_{SYSn}$−BP$_{SYSn-1}$/BP$_{SYSn-1}$)≧20%. A positive judgment made at Step SB9 indicates that the systolic BP values BP$_{SYS}$ of the patient have largely or significantly changed.

If a negative judgment is made at Step SB9, the current control cycle is ended, and the control goes back to Step SB1 and the following steps. On the other hand, if a positive judgment is made at Step SB9, the control goes to Step SB10 to judge whether one of the BP-measurement-start periods T$_B$ that is for one of the partial durations that includes the elapsed time ET when the change of the systolic BP values BP$_{SYS}$ has been detected at Step SB9, is longer than the period T$_B$ for the partial duration that precedes or follows the above one partial duration in the dialysis duration. That is, the control device 26 judges whether the change of the systolic BP values BP$_{SYS}$ has been detected, at Step SB9, in the partial duration for which the longer period T$_B$ is set based on the estimation that in the partial duration the BP values BP of the patient would be considerably stable. Regarding Patient No. 1, the control device 16 judges whether the current partial duration in which the change of the systolic BP values BP$_{SYS}$ has been detected at Step SB9 is the first or third partial duration in the dialysis duration.

If a negative judgment is made at Step SB10, the current control cycle is ended, and the control goes back to Step SB1 and the following steps. On the other hand, if a positive judgment is made at Step SB10, the control goes to Step SB11 corresponding to the modifying means 78. At Step SB11, the control device 26 modifies the set of BP-measurement-start periods T$_B$ and the corresponding set of partial durations that have been selected, input, or read at Step SA2, SA4, or SA5, such that the modified set of periods T$_B$ includes, for a predetermined partial duration which includes the elapsed time ET when the change of systolic BP values BP$_{SYS}$ has been detected at Step SB9, and has a predetermined length of time (e.g., 30 minutes before the time ET and 30 minutes after the same ET), a predetermined short period T$_B$ (e.g., 15 minutes), and a predetermined long period T$_B$ (e.g., 60 minutes) for at least one remaining partial duration (e.g., two partial durations preceding and following the partial duration including the elapsed time ET). The short period T$_B$ is shorter than the long period T$_B$ by a predetermined value (e.g., 45 minutes). The modified set of partial durations includes the partial duration including the elapsed time ET and the one or more remaining partial durations. The control device 26 stores, in the period-store area 42 of the memory device 28, the modified set of periods T$_B$ and the modified set of partial durations, in place of the set of periods T$_B$ and the set of partial durations that have been selected, input, or read at Step SA2, SA4, or SA5.

It emerges from the foregoing description that in the present embodiment, the patient identifying means 60 (Step SA1) identifies the current patient; the selecting means 62 (Steps SA2) selects, from the sets of BP-measurement-start periods T$_B$ for the patients, stored in the period-store area 42 of the memory device 38, the set of periods T$_B$ for the current patient identified by the patient identifying means 60; and the BP-measurement starting means 68 (SB6) starts the BP measuring means 70 (SB7) at each of the thus selected periods T$_B$. Thus, the present BP measuring apparatus 8 can be easily operated or used to automatically select, for each individual patient, the respective periods T$_B$ for the respective partial durations of the dialysis duration, including at least one specific partial duration in which. the BP values BP of the each patient may abruptly or largely change. Thus, the length of the specific partial duration in which the BP measuring operation is carried out at the short period T$_B$ can be minimized, which leads to reducing the burden exerted to the patient under the dialysis treatment and detecting quickly any abrupt decrease of the BP values of the patient.

In addition, in the present embodiment, the change detecting means 76 (Step SB9) detects the significant change of the BP values of the patient iteratively measured by the BP measuring means 70 and, if one partial duration including the elapsed time ET when the change of the BP values is detected by the change detecting means 76 is associated with the longer BP-measurement-start period T$_B$ than that associated with the preceding or following partial duration of the one partial duration in the blood-dialysis duration, the modifying means 78 modifies the set of BP-measurement-start periods T$_B$ and the set of partial durations associated therewith, such that the modified set of periods T$_B$ includes, for a predetermined partial duration including the elapsed time ET, a period T$_B$ shorter than the initial, longer period T$_B$, and stores, in the period-store area 42 of the memory device 38, the modified set of periods T$_B$, and the modified set of partial durations including the predetermined partial duration, in place of the initial set of periods T$_B$ and the initial set of partial durations. Thus, the present BP measuring apparatus 8 automatically modifies, based on the BP values measured by the BP measuring means 70, the periods T$_B$ and the partial durations stored in the period-memory area 42 of the memory device 38.

Next, there will be described a second embodiment of the present invention, by reference to FIGS. 7 and 8. The second embodiment also relates to a BP measuring apparatus which has the same hardware construction as that of the BP measuring apparatus 8 shown in FIG. 1. Accordingly, the same reference numerals as used for the first apparatus 8 will be used to designate the corresponding elements and parts of the present, second apparatus as the second embodiment, and the description and illustration thereof are omitted.

Figure 7:
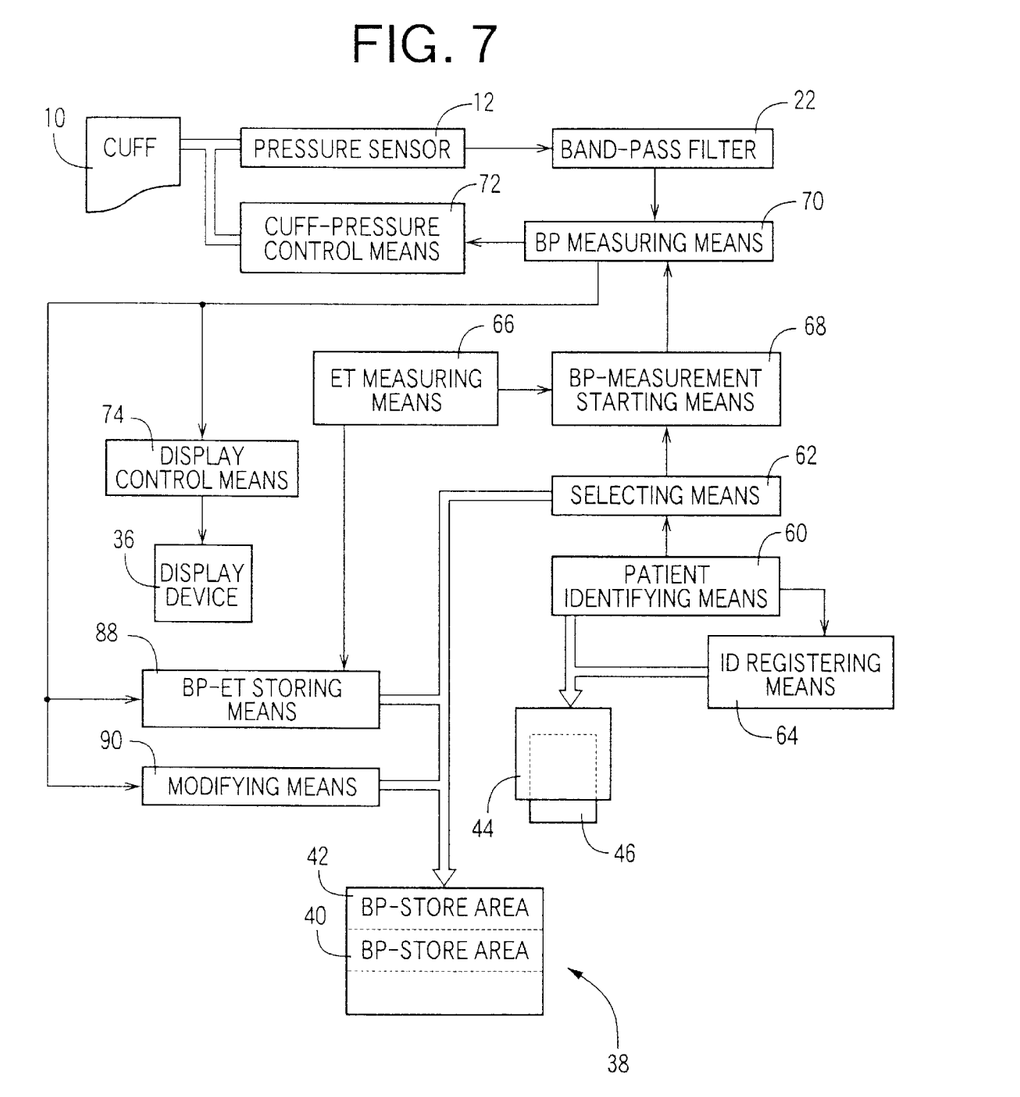
FIG. 7 is a diagrammatic view corresponding to FIG. 2, showing various functions of a control device 26 of another BP measuring apparatus as a second embodiment of the present invention.

FIG. 7 is a diagrammatic view of various functions of a control device 26 of the present BP measuring apparatus, which modifies each of a plurality of sets of BP-measurement-start periods TB and a corresponding one of a plurality of sets of partial durations, stored in a period-store area 42 of a memory device 38, in a manner different from the above-described manner in which the BP measuring apparatus 8 does. This difference will be described in detail, below.

The diagrammatic view of FIG. 7 differs from that of FIG. 2 only in that the change detecting means 76 and the modifying means 78 shown in FIG. 2 are replaced with a BP-ET storing means 88 and a modifying means 90 shown in FIG. 7.

The BP-ET storing means 88 stores, in a BP-store area 40 of the memory device 38, respective BP values BP (e.g., systolic BP values BP$_{SYS}$, diastolic BP values BP$_{DIA}$, mean BP values BP$_{MEAN}$, etc.) iteratively measured by a BP measuring means 70 from each patient, and respective elapsed times ET at which the BP values BP are measured by the BP measuring means 70. The modifying means 90 judges, when the current dialysis treatment which the current patient undergoes ends, if each of the BP values BP measured by the BP measuring means 70 and stored in the BP-store area 40 for the patient is lower than a reference value, and modifies the set of BP-measurement-start periods $T_B$ and the corresponding set of partial durations for the patient, such that the modified set of periods $T_B$ includes, for at least one predetermined partial duration including at least one elapsed time ET corresponding to at least one BP value judged as being lower than the reference value, a predetermined short period $BT_B$ for detecting any abrupt change of BP values. The modifying means 90 stores, in the period-store area 42, the thus modified set of periods $T_B$ and the thus modified set of partial durations, in place of the initial set of periods $T_B$ and the initial set of partial durations. For example, when one of the systolic BP values $BP_{SYS}$ stored in the BP-store area 40 for a patient is lower than a predetermined standard systolic BP value $SBP_{SYS}$, the modifying means 90 modifies the set of BP-measurement-start periods $T_B$ and the corresponding set of partial durations for the patient, such that the modified set of periods $T_B$ includes, for a predetermined partial duration including an elapsed time ET corresponding to the one systolic BP value $BP_{SYS}$ judged as being lower than the standard value $SBP_{SYS}$, a predetermined short BP-measurement-start period $BT_B$ and includes, for at least one remaining partial duration of the dialysis treatment, a predetermined long BP-measurement-start period $LT_B$ longer than the short period $BT_B$ by a predetermined value or time. The modified set of partial durations includes the predetermined partial duration including the elapsed time ET and the one or more remaining partial durations. The thus modified set of periods $T_B$ and modified set of partial durations are stored, in the period-store area 42, in place of the initial set of periods $T_B$ and initial set of partial durations.

Figure 8:
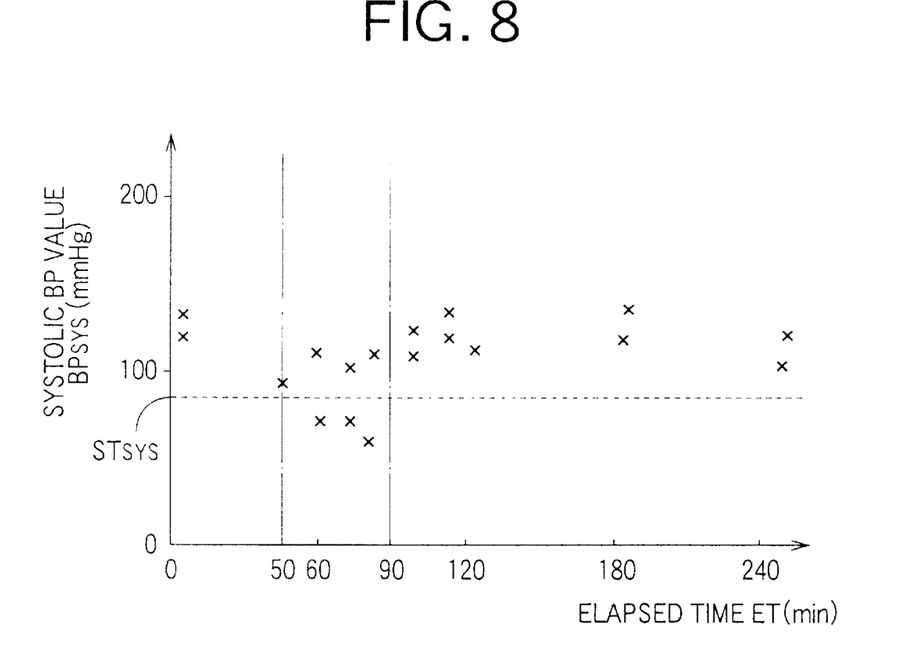
FIG. 8 is a view showing (a) a plurality of systolic BP values $BP_{SYS}$ stored in a BP-store area 40 of the memory device 38 of the BP measuring apparatus of FIG. 7, and (b) respective elapsed times ET when the systolic BP values $BP_{SYS}$ are measured by the BP measuring apparatus.

FIG. 8 shows a graph representing a relationship between respective systolic BP values $BP_{SYS}$ stored in the BP-store area 40 of the memory device 38 for a patient, and respective elapsed times ET at which the systolic BP values $BP_{SYS}$ are measured by the BP measuring means 70. In this case, the modifying means 90 judges whether each of the systolic BP values $BP_{SYS}$, indicated at symbols "x", is lower than the standard systolic BP value $SBP_{SYS}$, and allots the short BP-measurement-start period $BT_B$ (e.g., 15 minutes) for three consecutive predetermined partial durations including 60 minutes, 70 minutes, and 80 minutes when each systolic BP value $BP_{SYS}$ is lower than the standard systolic BP value $SBP_{SYS}$, and allots the long period $LT_B$ (e.g., 60 minutes) for the two remaining partial durations that precede and follow the three consecutive partial durations, respectively. Each of the three predetermined partial durations includes 10 minutes before the corresponding elapsed time ET corresponding to the systolic BP value $BP_{SYS}$ judges as being lower than the standard value $SBP_{SYS}$ and 10 minutes after the time ET. In summary, the modifying means 90 stores, in the period-store area 42, the long period $LT_B$ for the first partial duration from 0 to 50 minutes after the commencement of dialysis treatment, the short period $BT_B$ for the second partial duration from 50 to 90 minutes, and the long period $LT_B$ for the third partial duration from 90 minutes to the end of the dialysis duration.

It emerges from the foregoing description that like the first BP measuring apparatus 8, the second BP measuring apparatus can automatically select, for each individual patient, respective BP-measurement-start periods $T_B$ for a plurality of partial durations of the dialysis duration that include at least one specific partial duration in which the BP values of the each patient may largely decrease. In addition, the modifying means 90 modifies, based on the systolic BP values $BP_{SYS}$ stored in the BP-store area 40 of the memory device 38 for each individual patient and the elapsed times ET when the systolic BP values $BP_{SYS}$ are measured by the BP measuring means 70, the set of BP-measurement-start periods $T_B$ and the corresponding set of partial durations, stored in the period-store area 42 for the each patient, such that the modified set of periods $T_B$ include, for at least one predetermined partial duration including at least one elapsed time ET corresponding to at least one systolic BP value $BP_{SYS}$ judged as being lower than the standard value $SBP_{SYS}$, the short BP-measurement-start period $BT_B$. Thus, the second BP measuring apparatus can automatically optimize the sets of BP-measurement-start period $T_B$ including the short and long periods $BT_B$, $LT_B$, and the corresponding sets of partial durations. which are stored for the patients in the period-store area 42 of the memory device 38.

While the present invention has been described in its preferred embodiments, it is to be understood that the invention may otherwise be embodied.

For example, in each of the illustrated embodiments, the patient identifying means 60 identifies each patient based on the ID data recorded on the magnetic card 46 inserted in the card reader 44. However, the patient identifying means 60 may be so modified as to identify each patient based on ID data which are input through an input terminal (e.g., a keyboard) which is employed in the BP measuring apparatus. Alternatively, in the case where the BP measuring apparatus employs a volumetric-pulse-wave sensor which detects a volumetric pulse wave from a peripheral body portion of each patient, the patient identifying means 60 may identify the each patient based on the waveform of the volumetric pulse wave detected from the each patient. Moreover, the patient identifying means 60 may identify each patient based on his or her fingerprint.

In each of the illustrated embodiments, the ID data identifying each patient are recorded on the magnetic card 46 carried by the patient. However, the magnetic, card 46 may be replaced by a magnetic disc, an IC card, or a RAM card. In the latter case, the magnetic disc, ID card, or RAM card may function as the memory device 38 including the period-store area 42 and the BP-store area 40.

In each of the illustrated embodiments, the entire duration of blood-dialysis treatment is divided into three partial durations, and respective BP-measurement-start periods $T_B$ are allotted to the three partial durations. However, the total number of the partial durations is not limited to three, but may be two, four, or more. For example, for Patient No. 4 shown in FIG. 3, the dialysis duration is divided into four partial durations.

In each of the illustrated embodiments, the change detecting means 76 detects the significant change of the systolic BP values $BP_{SYS}$. However, the change detecting means 76 may be so modified as to detect a significant change of the diastolic or mean BP values $BP_{SYS}$, $BP_{MEAN}$.

In the second illustrated embodiment, the modifying means 90 modifies, based on the systolic BP values $BP_{SYS}$ stored in the BP-store area 40 of the memory device 38, the set of BP-measurement-start periods TB and the corresponding set of partial durations, stored in the period-store area 42 of the memory device 38. However, the modifying means 90 may utilize, for the above modification, the diastolic or mean BP values $BP_{SYS}$, $BP_{MEAN}$ stored in the BP-store area 40.

In the second illustrated embodiment, the modifying means 90 employs 15 minutes as the short BP-measurement-start period $BT_B$, and 60 minutes as the long BP-measurement-start period $LT_B$. However, the short and long periods $BT_B$, $LT_B$ are not limited to those times or values.

In each of the illustrated embodiments, the BP 34. measuring means 70 measures BP values of each patient according to the so-called oscillometric method. However, the BP measuring means 70 may be so modified as to measure BP values of each patient according to the so-called Korotkoff-sound method.

It is to be understood that the present invention may be embodied with other changes, modifications and improvements which may occur to a person skilled in the art, without departing from the spirit and scope of the invention defined in the appended claims.

What is claimed is:

1. An apparatus for iteratively measuring a blood pressure of a living subject who is undergoing a blood-dialysis treatment, comprising:

an inflatable cuff which applies a pressing force to a body portion of said subject;

a blood-pressure measuring device which measures a blood pressure of said subject by changing the pressing force of the cuff applied to the body portion of said subject;

a starting means for starting the blood-pressure measuring device at a predetermined period in a dialysis duration in which said subject undergoes the blood-dialysis treatment, so that the blood-pressure measuring device iteratively measures a blood pressure of said subject at the predetermined period;

a period memory device which stores, for a plurality of living subjects including said subject, a plurality of sets of predetermined periods each set of which comprises respective predetermined periods for a plurality of partial durations of the dialysis duration;

an identifying means for identifying said subject; and a selecting means for selecting, from the sets of predetermined periods stored in the period memory device, the set of predetermined periods for said subject, so that the starting means starts, in each of the partial durations of the dialysis duration, the blood-pressure measuring device at a corresponding one of the predetermined periods of the selected set, and the blood-pressure measuring device iteratively measures a blood pressure of said subject in said each of the partial durations of the dialysis duration at said corresponding one of the predetermined periods of the selected set.

2. An apparatus according to claim 1, further comprising:

a detecting means for detecting a change of the blood pressure values iteratively measured by the blood-pressure measuring device; and a modifying means for modifying, when the detecting means detects the change of the blood pressure values at an elapsed time in a first one of the partial durations of the dialysis duration that is associated with a longer predetermined period than a predetermined period associated with at least one of a second partial duration preceding the first partial duration, and a third partial duration following the first partial duration, the set of predetermined periods selected by the selecting means for said subject, such that the modified set of periods comprises. for a predetermined partial duration including said elapsed time, a period shorter than said longer predetermined period, said modifying means storing, in the period memory device, the modified set of periods in place of the selected set of periods.

3. An apparatus according to claim 1, further comprising:

a blood-pressure memory device which stores, for said subject, the blood pressure values iteratively measured by the blood-pressure measuring device in the dialysis duration, and respective elapsed times, after a commencement of the dialysis duration, at which the blood pressure values are iteratively measured by the blood-pressure measuring device; and a modifying means for modifying, when the blood pressure values stored in the; blood-pressure memory device in the dialysis duration for said subject comprise at least one blood pressure value lower than a reference value, the set of predetermined periods selected by the selecting means for said subject, such that the modified set of periods comprises, for at least one first predetermined partial duration including at least one elapsed time corresponding to said at least one blood pressure value, a first predetermined period shorter than a second predetermined period for at least one second partial duration of the dialysis duration other than said at least one first partial duration, said modifying means storing, in the period memory device, the modified set of periods in place of the selected set of periods.

4. An apparatus according to claim 1, wherein the period memory device stores a plurality of sets of identification data identifying said plurality of living subjects, respectively, such that the sets of identification data are associated with the sets of predetermined periods, respectively, and wherein the identifying means comprises:

an input device which is operable by said subject for inputting a set of identification; data identifying said subject; and judging means for judging whether the set of identification data input through the input device is identical with one of the sets of identification data stored in the period memory device, wherein when the judging means judges that the set of identification data input through the input device is identical with one of the sets of identification data stored in the period memory device, the selecting means selects, from the sets of predetermined periods stored in the period memory device, the set of predetermined periods associated with the set of identification data identifying said subject.

5. An apparatus according to claim 2, wherein the detecting means comprises:

calculating means for calculating an absolute value of a proportion of an amount of change of each of the blood pressure values iteratively measured by the blood-pressure measuring device, from a preceding blood pressure value thereof, relative to the preceding blood pressure value; and judging means for judging whether said absolute value is greater than a reference value, wherein when the judging means judges that said absolute value is greater than the reference value, the detecting means detects said change of the blood pressure values.

* * * * *